United States Patent [19]

Gracovetsky

[11] Patent Number: 4,664,130
[45] Date of Patent: May 12, 1987

[54] METHOD AND EQUIPMENT FOR THE DETECTION OF MECHANICAL INJURIES IN THE LUMBAR SPINE OF A PATIENT

[75] Inventor: Serge Gracovetsky, St-Lambert, Canada

[73] Assignee: Diagnospine Research Inc., St-Lambert, Canada

[21] Appl. No.: 742,037

[22] Filed: Jun. 6, 1985

[51] Int. Cl.$^4$ ............................................. A61B 5/10
[52] U.S. Cl. ....................................... 128/781; 128/733
[58] Field of Search ............... 128/774, 781, 733, 653, 128/660; 33/511-512

[56] References Cited

U.S. PATENT DOCUMENTS

| 3,608,541 | 9/1971 | Hall | 128/781 |
| 4,108,164 | 8/1978 | Hall, Sr. | 128/781 |
| 4,202,355 | 5/1980 | Loeffler | 128/781 X |
| 4,213,466 | 7/1980 | Stulen | 128/733 |
| 4,373,532 | 2/1983 | Hill et al. | 128/660 |
| 4,506,676 | 3/1985 | Duska | 128/653 |

FOREIGN PATENT DOCUMENTS

| 0140681 | 5/1985 | European Pat. Off. | 128/774 |
| 1564781 | 4/1969 | France | 128/774 |
| 2491323 | 4/1982 | France | 128/774 |
| WO81/01506 | 6/1981 | PCT Int'l Appl. | |
| 0772529 | 10/1980 | U.S.S.R. | 128/781 |
| 0933077 | 6/1982 | U.S.S.R. | |

OTHER PUBLICATIONS

Atkinson et al.; "Closed Circuit TV Movement Detector"; Med. & Biol. Eng. and Comput., vol. 19, No. 6, 11-1981, pp. 789-791.

Anderson et al.; "A Combined Flexi-Rule Hydrogoniometer for Measurement of Lumbar Spine and Its Sagittal Movement"; Rheumatology and Rehab., vol. 14, No. 3, 1975, pp. 173-180.

Terekhov; "Measuring Man's Stability of Stance"; J. of Clin. Eng., 1-3/1979, pp. 61-65.

Perritt et al.; "A Simple, Inexpensive 8-Channel Multiplexer for Electromyography in Human Locomotion"; Med. and Biol. Eng., 1-1976, pp. 104-106.

Primary Examiner—Kyle L. Howell
Assistant Examiner—Angela D. Sykes
Attorney, Agent, or Firm—Robic, Robic & Associates

[57] ABSTRACT

A method and an equipment for the detection of a mechanical abnormality or injury in the lumbar spine of a patient and for the identification of this abnormality or injury as being of the compression or torsion type. In a first step, any variation of the lumbar curve of the patient is measured using a combined visual and an electromyographic (EMG) technique. Then, any discrepancy or assymetry is detected in said measured variation of lumbar curve. In practice, the absence of any variation or the detection of any discrepancy or assymetry in the case where a variation is measured, is indicative of the presence of a mechanical abnormality or injury of the lumbar spine of the patient, and of the nature of this particular abnormality or injury.

23 Claims, 19 Drawing Figures

ERECTORES SPINAE 10KG. LIFT

FIG. 9

METHOD AND EQUIPMENT FOR THE DETECTION OF MECHANICAL INJURIES IN THE LUMBAR SPINE OF A PATIENT

BACKGROUND OF THE INVENTION (a) Field of the Invention

The present invention relates to a non invasive method for the detection of a mechanical abnormality or injury in the lumbar spine of a patient.

The invention also relates to a method and to an equipment for the detection of mechanical injuries in the lumbar spine of a patient and for the identification of these injuries as being of the compression and/or torsional type.

(b) Brief Description of the State of the Art

It is well known in the medical art that common back disorders have a mechanical etiology. It is also well known from pathological studies that there are two common patterns of disc injury which correspond to two different types of mechanical failure of the spine.

The first type of common injury hereinafter referred to as <<compression injury>>, usually starts by a central damage to the disk with fracture of varying magnitude of the end plates of the adjacent vertebrae, sometimes followed by injection of part of the nucleus into the vertebral body. In this particular case, the injured end plate permits the invasion of the avascular nucleus and of the avascular inner portion of the annulus by granulation tissue ingrowing through the fractured end plate, such an invasion leading to gradual destruction of the avascular nucleus and inner annulus. In the early stages, the facet joints of the vertebrae are not affected and the outer annulus survives while the center portion of the disc is destroyed. With progression, the disc loses its thickness while the outer layer of the annulus remains relatively well preserved. With lost of this thickness, the facet joint subluxates and develops a moderate degree of osteoarthritis.

Usually, the fracture of the end plate of a vertebra is an undisplaced fracture of cancellous bone which heals rapidly. The symptoms are short lived, typically lasting two weeks. The facet joint arthritis appears late. At this stage, symptoms may also arise from the reduction in size of the spinal canal (lateral or central spinal stenosis).

The other type of common injury hereinafter referred to as <<torsional injury>>, is characterized by a damage to the annulus occuring simultaneously with a damage to the facet joints. The annulus is avulsed from the end plate and its laminae become separated while the central disk and the end plate remain intact. At the later stage, the annulus develops radial fissures while the nucleus remains relatively untouched. The changes in the facet joints are severed with massive joint destruction and osteophytosis similar to hypertropic arthritis. Relatively late in the process, there may be changes in the end-plates and central disks, with consequent collapse of the articular surfaces and chronic synovitis.

In this particular case, the basis injury is to collagenous ligamentaous tissue which requires six weeks to regain 60% of its strength. Because the injury involves both the disk and facet joints, it is more difficult for the joint to stabilize itself and recurrence is frequent. The condition is progressive and may lead to spinal stenosis, instability and degenerative spondilolisthesis.

Tests conducted in laboratory have shown that a compression injury is easily produced by compressing a joint between 2 Mpa to 6 Mpa. A torsional injury can be seen with as little as 2 to 3 degrees of forced rotation requiring only 22 to 33 Newton-meters of torque.

Statistically, in a group of patients suffering from back disorders, 64% exhibit torsional injuries whereas 35% exhibit axial compression injuries. Statistics have also shown that torsional injury occurs mainly at the $L_4$-$L_5$ level (almost 76% of forth joint problems are of torsional nature). Statistics have also shown that almost 98% of the compression injuries occur at the $L_5$-$S_1$ level. Statistics have further shown that double injuries where the joint is injured both in compression and torsion, occur in 22% of the cases, invariably at the $L_5$-$S_1$ level.

The following Table I reflects the probabilities of injuries among patients complaining from backache and sciatica, or sciatica alone. As can be seen from this Table, the important frequency of torsional injury cannot be overlooked. As can also be seen, the probability of a third type of injury giving symptoms is very remote.

TABLE I

CLINICAL DETERMINATION OF THE VARIOUS PROBABILITIES OF INJURIES

| JOINT | P (injury) | P (compression) | P (torsion) |
|---|---|---|---|
| $L_5/S_1$ | 47% | 98% | 22% |
| $L_4/L_5$ | 47% | 1%< | 76% |
| $L_3/L_4$ | 5%< | 1%< | 1%< |
| $L_2/L_3$ | 1%< | 1%< | 1%< |
| $L_1/L_2$ | 1%< | 1%< | 1%< |
|  | 100% | 100% | 100% |

It is also well known that health professionals are trained to use symptoms in the determination of diagnoses, the large numbers of known symptoms being quite naturally associated with a large number injuries and diagnoses. Unfortunately, as can be understood from the above short description of the pathology in the case of back disorders, both the compression and torsion injuries give rise to identical symptomology. Hence, symptoms cannot be used to diagnose a type of injury because identical symptoms may arise from different injuries.

It is also well known in the art that low back pain is the leading cause of disability in North America today, affecting from 8 to 9 million people. It is the most common disability in persons under the age of 45 and the third only after arthritis and heart disease in those over 45. It is also estimated that two of three persons will have a low back pain at some time of their lifes, usually between the ages of 20 and 50. The fact that problems are so common in people of working age is not coincidental. Indeed, most of the back problems are work-related. As the injury caused by a certain task cannot be identified from the patient's symptoms, it is of course not possible to relate directly a given task to an injury mode, although such a relationship is central to the definition of tasks that will not injure a specific worker.

The economic effects of back pain and injuries are staggering. Back problems are second only to the common cold as a cause of absenteeism in the industry. It is moreover responsible for 93 million lost workdays every year and is a leading cause of reduced work capacity. Hence, an incentive for prevention of back injury is very large.

In order to unequivocally relate a given task to a given injury in the absence of any measurement of the effect of the task on a given joint, it has already been suggested to use mathematical and/or biochemical model of spine, like the one suggested by J. M. Morris et al in their article <<The Role of trunk in stability of the spine>>, J. Bone and Joint Surg., 43A, 1961. However, a major problem with the known models of spine, including the widely used model of J. M. Morris et al, is that they do not truly reflect the physiological behaviour of the spine over the full range of capacity.

Thus, by way of example, the model of J. M. Morris et al which assumes, as fundamental hypothesis, that the moment generated by the body weight and any external load carried by the patient is balanced by the combined action of the erectores spinae and the intra-abdominal pressure, is a very poor representation of physiological behaviour which is not supported by observations. By way of example, such a model predicts a total failure of the spinal mechanism at about one fourth of the known potential of a healthy spine.

The major reason why all of the models known to the inventor are defective is essentially because they give an incomplete representation of the actual anatomy of a human being. It is true that a moment-supporting member is required in such a model but this cannot be the abdominal pressure only, as suggested by J. M. Morris et al.

SUMMARY OF THE INVENTION

A first object of the present invention is to provide a non invasive method for the detection of a mechanical abnormality or injury in the lumbar spine of a patient, which method makes use of a combined visual and electromyographic technique.

This first object of the invention derives from an observation made by the inventor that a healthy spine is characterized by its ability to flex smoothly in any plane. Hence, an injury to any joint of the spine will always result in a reduced flexing range of motion of the spine.

Based on this particular observation, the noninvasive method according to the invention for the detection of a mechanical abnormality or injury in the lumbar spine of a patient, comprises the steps of:

measuring any variation in the lumbar curve of the patient while the same is performing a physical test, using a combined visual and electromyographic technique; and detecting any discrepancy or assymmetry away from the average response of a group of normal healthy persons in said measured variation of lumbar curve;

wherein the absence of any variation or the detection of any discrepancy or assymmetry in the measured variation when compared with the average, is indicative of the presence of a mechanical abnormality or injury in the lumbar spine of said patient.

It should be noted that in the present specification, <<non invasive>> method means a method where no invasive tools such as X-rays, needles and the like are used for collecting the physiological data necessary for detecting the presence of a mechanical abnormality or injury.

Another object of the invention is to provide a method and an equipment for the detection of mechanical injuries in the lumbar spine of a patient and for the identification of said injuries as being of the compression and/or torsional type, which method and equipment derive from a new representation of the anatomy of a spine which itself derives from the above mentioned observations.

This new representation of the anatomy of a spine from which derives the invention, advantageously includes the posterior ligamentous system as possible support for any moment generated onto the spine by the body weight and any external load carried by the patient. This new representation of the anatomy of the spine also takes into account the extensors of the hip, which have the bulk and the lever arm necessary to supply all the moment requirements to flex the spine.

In greater details, this new representation of the anatomy of a spine is based on the fact that, under normal circumstances, most of the motion of an unloaded individual flexing forward from zero upright down to about 45°, is due to spinal flexion. From 45° to full flexion, the motion is mostly due to the rotation of the pelvis at the hips.

In the range of 0° to 45°, the posterior midline ligament system is inactive and, in its place, the erectores spinae and/or the abdominal muscles support the moment due to the body weight. From 45° to full flexion, this moment can be supported by the midline ligament system without muscular activity. This relaxation phenomenon from muscular to ligamentous support was already noted in the art by W. F. Floyd et al in their article <<The Function of the Erector Spinae Muscles in certain Movements and Postures in Man>>, J. Physiology, volume 129, pp. 184–203, 1955.

Using electromyographic (EMG) measurements, W. F. Floyd et al clearly saw a relation between the moment to be supported and the angle of forward flexion, and realized the meticulous coordination of muscle, ligament and joint movement. They hypothetized that in the case of injury to an intervertebral joint, this delicate coordination will be upset and this would be reflected in change of the E.M.G. pattern. Then, they embarcated on an E.M.G. study and tried to compare statistically the E.M.G. pattern of normal individuals to that of those with common back problems in the performance to a standardized simple weight lifting task. However, they gave up after testing 140 cases because the results were inconsistent.

In accordance with the present invention, it is taken from granted that the pelvis acts as a <<supporting base>> for entire spine. It is also assumed that any healthy person will perform a task in such a way as to substantially minimize and equalize the stress at each invertebral joint. Moreover, it is assumed that the main power for a lift is generated by the extensors of the hip, such as the Gluteus Maximae.

The moment generated by these muscles is transmitted to the upper extremities by the trunk musculature and the posterior ligamentous system (PLS) which, for the purpose of this discussion, is composed of the midline ligament and the lumbodorsal fascia. Regardless of the inclination of the trunk, the moment generated by the extensors of the hip must equal the sum of the moment generated by the trunk musculature and PLS. Therefore, for any given hip extensor moment one can find an infinite number of combinations to distribute this moment between trunk muscles and the PLS.

Because of the reserve capacity in performing a small weight lift, a normal individual may select a combination of ligaments and muscles which is not optimum from a stress minimization point of view. However, the reserve is reduced in the presence of injury. The option of selecting a non-optimum strategy is also reduced.

Therefore one can expect a certain amount of variation in EMG pattern in a normal individual and a very limited variation in those with injury.

Assuming that the distribution of moment between ligaments and muscles is controlled by the requirement that stress be minimized and equalized at all lumbar joints, stress at one intervertebral joint will be defined as the ratio of the resultant compressive force acting perpendicular to the bisector of the disk to the area of the disk. In general except in the normal erect stance, when muscles are used, the stress is higher than when either ligament systems are used, because the lever arms of the ligament systems are longer than those of any of the muscles. The midline ligament system can be activated only when the spine is sufficiently flexed. The hip/-shoulder angle $\alpha$ at which this ligament takes up tension is called $\alpha_o$, which is about 45 degrees for no load. This ligament system is strong enough to support the heaviest lift and hence, when this ligament system is activated, the spinal musculature is no longer required and therefore the muscles are electrically silent. As aforesaid, this is the muscle relaxation phenomenon observed by W. F. Floyd et al.

The thoracodorsal fascia can be activated by the contractions of the abdominal muscles, in particular the internal oblique and *T. abdominis*, which exert a pull at its lateral margin only when the abdominal pressure is at sufficient value to maintain a rounded abdominal cavity. This ligament system can therefore be activated for any angle of flexion. This is an essential difference when compared to the midline ligament.

Based on such a new representation of the anatomy of a spine, the method according to the invention as claimed hereinafter for the detection of mechanical injuries in the lumbar spine of the patient and the identification of these injuries as being of the compression and/or torsional type, comprises the steps of:

(a) fixing a first pair of surface-electrodes onto the back of the patient in a bilateral and symmetrical manner with respect to his spine in the lumbar zone, in order to record the electromyographic (EMG) activities of erectores of said patient;

(b) fixing a second pair of surface-electrodes in a bilateral manner onto the triangles of Petit of said patient in order to record the EMG activity of the Internal Oblique of said patient;

(c) fixing a third pair of surface-electrodes in a bilateral manner behind the thighs of said patient in order to record the EMG activity of the hip extensors of said patient;

(d) measuring with said surface-electrodes the muscle activity of the patient while he is flexing forward in the median plane and pulling up a small load, and independently recording the EMG activities measured by each of said surface electrodes as a function of time;

(e) simultaneously to step (d), measuring the angle of flexion $\alpha$ of the patient, said angle $\alpha$ being dihedral angle between a plane passing through the hips and shoulders of said patient and a vertical plane parallel to the frontal plane of said patient, and recording said angle $\alpha$ as a function of time;

(f) processing the recorded EMG activities measured on the patient to calculate the relative variations in activities of the erectores versus the hip extensors (E/H ratio) and of the Internal Oblique versus the hip extensors (A/H ratio) and plotting said E/H and A/H ratios versus $\alpha$; and (g) further processing said recorded EMG activities measured on the patient to calculate the amount of assymmetry <<a>> between the recorded EMG activities measured on the right side of the patient and the recorded EMG activities measured on the left side of said patient, and plotting <<a>> versus $\alpha$;

wherein the observation of a high A/H ratio which corresponds to an extensive use of the abdominals, with the simultaneous observation of a significant delay in the detection of a sharp variation of the E/H ratio at a given angle $\alpha$ or of no variation at all of said E/H ratio when the patient is pulling up the small load, indicate that the patient cannot relax his erectores at the beginning of the lift, such a refusal indicating in turn that the patient has difficulty to flex his spine and therefore has a joint injury of the compression or torsional type; and wherein the observation of a significant variation of <<a>> when $\alpha$ varies, that is during the lift of the small weight, indicates that the joint injury in the lumbar spine is of the torsional type.

In order to make the interpretation easier, the method according to the invention may also comprise the additional steps of:

(h) measuring the lumbo-sacral angle $\lambda$, said angle $\lambda$ being the angle between the bissector of the $L_5$-$S_1$ disc and the bissector of the $T_{12}$-$L_1$ disc of the patient; and (i) using said measured angle $\lambda$ to determine the angle $\alpha_o$ at which the lordosis of the patient's spine is eliminated when said patient is pulling up the small load, said elimination corresponding to a switching made by the patient of the balancing of the load being pulled up from his muscles to his ligaments in order to reduce the stress level which the spine has to sustain, said angle $\alpha_o$ which is the very one at which a sharp variation of the E/H ratio should be detected, being the angle $\alpha$ at which the variation of the rate of change of $\lambda$ versus $\alpha$ is maximum.

The equipment according to the invention for use to carry out the above method comprises:

a first pair of surface-electrodes fixable onto the back of the patient in a bilateral and symmetrical manner with respect to his spine in the lumbar zone in order to record the electromyographic (EMG) activities of the erectores of said patient;

a second pair of surface electrodes fixable in a bilateral manner onto the triangles of Petit of the patient in order to record the EMG activity of the Internal Oblique of said patient;

a third pair of surface electrodes fixable in a bilateral manner behind the thighs of the patient in order to record the EMG activity of the hip extensors of said patient;

means for measuring the EMG activity of the patient with said pairs of surface electrodes while he is flexing forward in the median plane and pulling up a small load;

means for independently recording the EMG activity measured by each of said surface electrodes as a function of time;

means for measuring the angle of flexion $\alpha$ of the patient, said angle $\alpha$ being the dihedral angle between a plane passing through the hips and shoulders of the patient and the vertical plane parallel to the frontal plane of said patient;

means for recording the measured angle $\alpha$ as a function of time;

means for processing the recorded EMG activities measured on the patient to calculate the relative variations in activities of the erectores versus the hip extensors (E/H ratio) and of the Internal Oblique versus the hip extensors (A/H ratio);

means for plotting said E/H and A/H ratios versus $\alpha$;

means for further processing the recorded EMG activities measured on the patient to calculate the amount of assymmetry $<<a>>$ between the recorded EMG activities measured on the right side of the patient and the recorded EMG activities measured on the left side of said patient; and means for plotting $<<a>>$ versus $\alpha$.

As can be easily understood, the method according to the invention for determining the mechanical condition of the lumbar spine and the extend of breakdown of its mechanism, may be used to classify spines according to their efficiency and thus help in matching jobs with spine conditions to avoid needless exposure to injury, thus reducing the risk of said injury. As a result, the overall cost of medical treatment should be reduced. Moreover, the method according to the invention can be used as diagnosis tool to determine an optimal method of rehabiliation in the case of an injured spine, by either conservative methods or surgical repair.

The method according to the invention is particularly interesting in that it can be carried out at low cost and thus be used extensively for the screening of individuals with common low back problems in order to diagnose the exact mechanical fault for the purpose of prognostication, treatment, effects of treatment and rehabilitation. The method according to the invention may also be used to assess the individual capacity to perform a given task or, inversally, to assess a particular job for its risk to the individual. It may further be used to assess insurance of risk and compensation and to select fitness or athletic training programs.

BRIEF DESCRIPTION OF THE DRAWINGS

The invention and its advantages will be better understood with reference to the following, non restrictive description of a preferred embodiment thereof, given in connection with the accompanying drawing in which:

FIG. 3($a$), ($b$) and ($c$) are schematic views of a patient in flexed position and/or of his spine, in which views are defined the angle of flexion $\alpha$, the lumbar curve angle LC and the lumbo-sacral angle $\lambda$;

FIGS. 5($a$) and ($b$) are non-processed and processed E.M.G. signals of the erectores spinae of a patient versus time;

FIG. 5($c$) is a representation of the processed E.M.G. signal of FIG. 5($b$) versus $\alpha$;

FIG. 6($a$) and ($b$) are representations of the variations of the ratios E/H and A/H versus $\alpha$ in the case of a healthy patient and a patient having a compression injury, respectively;

FIGS. 7($a$), ($b$), ($c$), and ($d$) are representations of a heathy E.M.G. response of the left erectores spinae of the patient as a function of the load to be lifted;

FIGS. 8($a$), ($b$), and ($c$) are examples of abnormal E.M.G. responses; and

DESCRIPTION OF A PREFERRED EMBODIMENT

A. THEORETICAL CONSIDERATIONS

As aforesaid, the non representation of the anatomy of the spine which is used in accordance with the present invention includes the pelvis as a supporting base for the entire spine and assumes as fundamental hypothesis, that any healthy person will perform a task in such a way as to substantially minimize and equalize the stress or some components of this stress such as the compression stress component or the shear stress components at each intervertebral joint. In other words, all healthy persons are expected to perform a task in such a way as to minimize and equalize the stress at each joint.

Of course, this does not mean that all healthy persons will execute a lift in an identical manner. Differences in individual characteristics will affect the overall response. However, it is essential to understand that the overall response of any healthy individual will reflect the same overall objectives, namely:

(1) lifting the weight; and (2) minimizing and equalizing the stress at each intervertebral joint.

Because the objective of stress equalization and minimization is theoretically independent of the task, it is reasonable to analyze the problem by selecting a task that will simplify computations and generating enough force at the intervertebral joints to make measurement possible. For this reason, the choice of a weight lifting as a model has been made, although such a choice is not restrictive.

Figure 2:
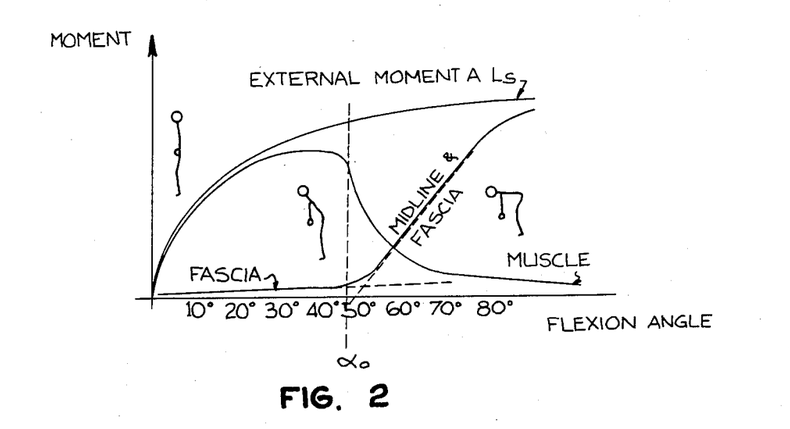
FIG. 2 is a representation of the moments generated by the muscles and ligaments as a function of the angle of flexion in the case of an healty patent lifting a small weight.

The coordination between the muscles, the ligaments and the geometry in the case of a symmetrical weightlifting is illustrated in FIG. 2 of the drawings. As can be seen, from 0° to about 40°, the external moment at the level of lumbar vertebra L5 is essentially balanced by the action of the muscles. During this first arc of motion, the spine unfolds or straighten out. Hence, the midline ligament which was slack when the subject was upright, becomes progressively tightened. During this operation, the patient may contract his abdominal muscles thereby allowing his fascia to contribute to the lift.

At approximatively 40°, the spine is sufficiently flexed to permit the midline ligament to be set under tension. When this is done, the power of the hip extensors can be transmitted directly to the upper extremities. Hence, there is no need for the activity of the erectores spinae. In this connection, it is important to realize that for a given lift, the use of the posterior ligamentous system (PLS) instead of the erectores spinae will always result in a lower level of stress at joint when the spine is bent.

It can be appreciated that a stiff spine such as sometimes seen after surgery, will not permit the full use of the posterior ligamentous system. Consequently, the erectores spinae will have to work more, and therefore increase the level of stress that the spine must take with the attendant higher probability of failure.

When the spine has been fully unfolded and the patient continues bending forward in the 40°-80° range, the motion will be executed by rotating the pelvis. As the weight to be lifted increases, the angle $\alpha_o$ at which the lordosis of the patient's spine is eliminated, moves toward O. Such an elimination of lordosis corresponds to a switching by the patient of the balancing of the load being pulled up from his muscles to his ligaments in order to reduce the stress level which the spine has to sustain. In other words, the spine flexes earlier and the midline ligament comes earlier into tension.

As can be easily understood, the moments created by all the forces intervening at each intervertebral joint must be balanced at all times during the flexion. In other words, the moment generated by the hip extensors must equal to the moment generated by the erectores, plus the moment generated by the abdominals acting on the lumbo-dorsal fascia, plus the moment generated by the midline ligament. This particular relation can be written as follows:

$$H = E + A + L \quad (I)$$

where:
 H is the moment generated by the hip extensors;
 E is the moment generated by the erectores;
 A is the moment generated by the abdominals; and
 L is the moment generated by the midline ligament.

In practice, the muscular activity of the patient can be monitored by recording the electromyographic (EMG) activities of the muscles of the patient by means of a plurality of surface electrodes. The use of EMG measurements for the calculation of the moment or force generated by a muscle is often subject to criticism because the relation between the EMG activity and the actual force of a muscle is very complicated (such a relation depends upon the velocity of muscle contraction and muscle length amongst other things). It should be noted however that, for the purpose of the present analysis, it is not necessary to know the precise relation between the EMG and the actual muscle force, as long as it is monotonous. The higher will be the force, the higher will be EMG. In this connection, it is admitted in the prior art that this relation is linear provided that the muscle activity is not excessive. By non excessive, there is meant a rather slow lift (2-3 sec) and a weight to be pulled up lower than 25 kg.

Therefore, the ratio of the EMG activity of two muscles will be proportional to the ratio of the moments generated by these two muscles. In the particular cases of the erectores and hip extensors of a patient, this relation can be written as follows:

$E/H = K \cdot$ integrated EMG (erectores)/integrated EMG (hip extensors)

where K is a constant.

It should be noted that, in the above equation (I), it is not necessary to measure the EMG, of all the hip extensors inasmuch as the activity of the Gluteus Maxima is known to be proportional to the moment generated by the all of said hip extensors. As a result, mere measurement of the activity of the Gluteus Maxima will be sufficient.

It should also be noted that the ratio E/H or the ratio A/H are functions of the angle of flexion $\alpha$.

(a) Case of an healthy individual

For a small load, an healthy (normal) individual may satisfy the above mentioned equation (I) in an infinite number of ways by distributing H between E, A and L. The equation (I) can however be simplified by asking the patient to execute the lift while relaxing his abdominals. In this particular case, the patient may be permitted to listen to the EMG activity of his abdominals by biofeedback to improve the measurement.

Figure 6A:
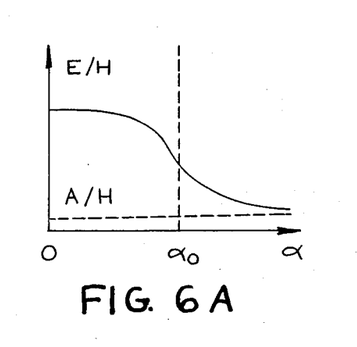

Experiences conducted by the inventor on healthy patients have shown that the load will be picked up while the spine is fully flexes with all muscles silent. In this particular case which is exemplified in FIG. 6(a):

$$E = A = 0$$

$$H = L$$

and $$E/H = 0$$

As a patient straightens up, the musculoskeletal system shifts the balancing of the load from the ligaments to the erectores. Hence:

$$A = L = 0$$

$$E = H$$

and $$E = k$$

The transition of the ratio E/H from 0 to k occurs during the lift at the critical angle $\alpha_o$.

In practice, it is not necessary to identify as such the angle $\alpha_o$. However, in order to better interpret the EMG data and the resulting E/H and A/H ratios, it may be interesting to identify this angle $\alpha_o$ choosen by the patient to switch the balancing of the load from his ligaments to his muscles (or vice versa).

As can be seen in FIG. 6(a) the ratio of the integrated EMG activities of the erectores versus the hip extensors varies from 0 to k with a transition (inflexion point) occurring at $\alpha_o$. It is interesting to note that the value of k is irrelevant to the interpretation of the curve.

(b) Case of a patient with a compression injury

A compression injury prevents a patient from fully flexing his spine. Therefore, the patient cannot efficiently use his midline ligament to balance the load and he must rely on his erectores and for his fascia to do so. However, it is known that to reduce compression and therefore pain at the intervertebral joint, the patient must reduce the activity of his erectores spinae as much as possible. As a result, a patient obliged to lift a load will delay the increase of the action of the erectores as long as he can by using the abdominals to tighten his fascia.

The activity of the abdominals can be monitored by installing surface electrodes over his triangles of Petit, where the activity of the Internal Obliques is directly measurable. The External Obliques are theoretically not relevant to the determination of all of the abdominals and therefore of the fascia, since these muscles fire substantially at the same time as the Internal Obliques and since both muscles are monitored bilaterally.

It is known that the extensor moment generated by the fascia when the same is tightened by the abdominals, depends on the specific arrangement of the ligament fibers, which arrangement is not known for a specific individual. This however is not important because the conversion factors of the lateral pull of the muscles of the fascia into a longitudinal tension of the spinous processes can be shown from geometrical consideration to increase when the angle of flexion increases. As a result, the relation of the measured EMG activity of the abdominals to the force of moment generated by the fascia due to the activity of these abdominals is monotonous and the same comments as above applies thereto.

Figure 6B:
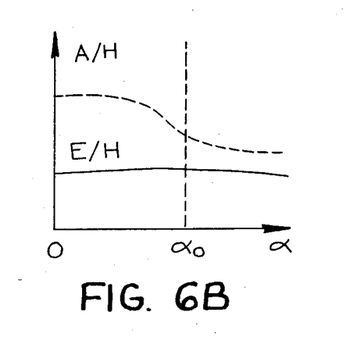
Figure 7A:
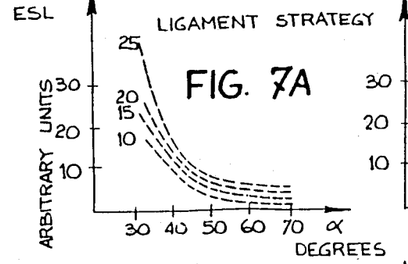
Figure 7B:
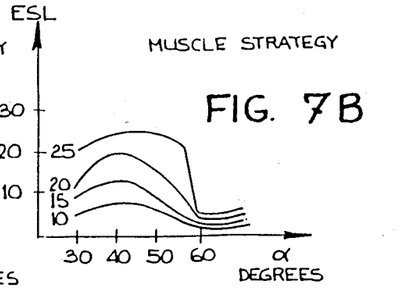
Figure 7C:
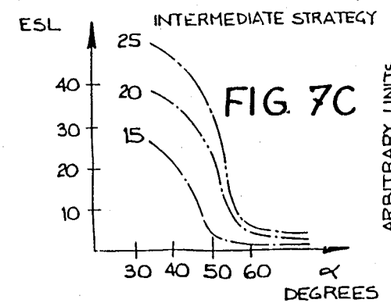
Figure 7D:
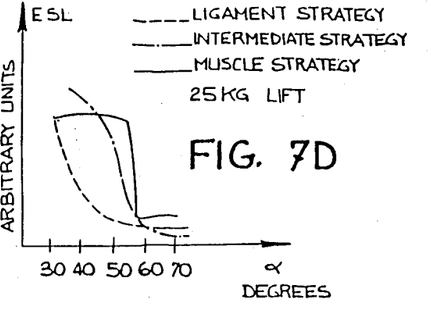

As can be seen in FIG. 6(b), the variation of E/H and A/H ratios in the case of a patient suffering a compression injury is markedly different from the one of an healthy patient. In this particular case, the relative activity of the abdominals versus the Gluteus Maxima (hip extensors) is of interest. It is apparent that the differences between the variation of E and A permits to distinguish between a normal spine and a spine with the compression injury. It should be noted that some patients will not be able to flex their spine at all. In this particular case, there will be no inflexion point in the curve shown in FIG. 6(b).

Once again, the angle of flexion $\alpha_o$ at which the lordosis is eliminated, can be separately measured in order to facilitate the interpretation of the curve. As shown in FIG. 7, the angle $\alpha_o$ is the reduced as the weight to be pulled up is increased. However, the variation of the EMG activity is not random scatter. As a result, the interpretation of the EMG will be fully determined by the knowledge of the angle $\alpha_o$.

(c) Case of a patient with a torsion injury

The determination of a torsion injury is related to the problem of asymmetry of the intervertebral joint. EMG measurements on volunteers with electrodes placed symmetrically on both sides of the spine have clearly shown that in some instances, there are true differences in the electrical activity between the right and left sides of the patient. A factor explaining these references is structural asymmetry.

Asymmetry of an intervertebral joint may reflect an asymmetric shear stress, and the degree of asymmetry reflects the differences in shear stress between right and left sides of the joint. The disk does not have the structural design to support shear stress. The obvious protective mechanism will be (1) an asymmetric facet joint and (2) an asymmetric muscular response.

The differences in EMG activities between the right (R) and left (L) sides of the spine are due to a variety of factors such as the resistance of the skin, the variability of the muscles motor points, and the general asymmetry of the patient. When there is no asymmetry, R is equal to L. If we assume that there is a constant gain difference between R and L because of asymmetric structure, then this difference can be identified. The R and L integrated activity signals can be collected at each millisecond. The sum of the square of all the (R−aL) can be obtained and minimized with respect to $<<a>>$. The value of this parameter $<<a>>$ which, in the ideal case of perfect asymmetry is equal to 1, characterizes the irreducible asymmetry between R and L and is arbitrarily assigned to describe the asymmetry of the joint.

In the absence of any torsional injury, the asymmetry of the joint will be constant during the lift. In other words, parameter $<<a>>$ will be constant for all the angle of flexion $\alpha$. This, in practice, has been confirmed by the inventor in the course of his preliminary experiments.

In the presence of a torsional injury, the asymmetry of the joint will increase with the load because the joint will rotate as the spine flexes, and the compression stress will increase. For a given weight to be lifted up, the compression stress on any joint is minimum in the erect position and maximum for full forward flexion. Hence parameter $<<a>>$ is not constant and depends upon the flexion angle $\alpha$ and upon the external weight to be lifted. The variation of $<<a>>$ during the lift characterizes the degree of torsional injury.

B. EQUIPMENT

Figure 1:
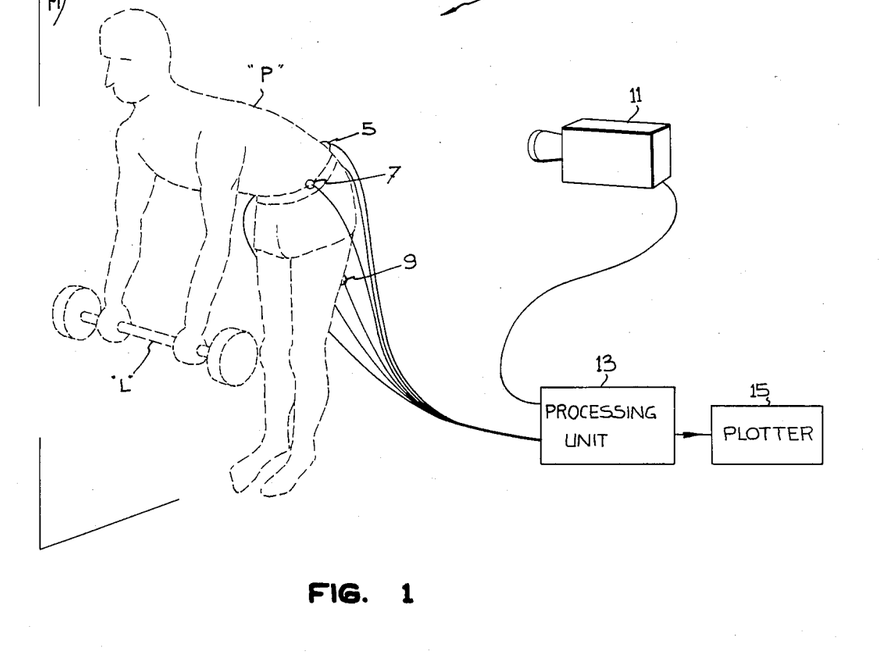
FIG. 1 is a schematic view of a non-invasive equipment for the detection of a mechanical abnormality or injury in the lumbar spine of the patient and the identification of its abnormality or injury as being of the compression or torsional type.
Figure 9:
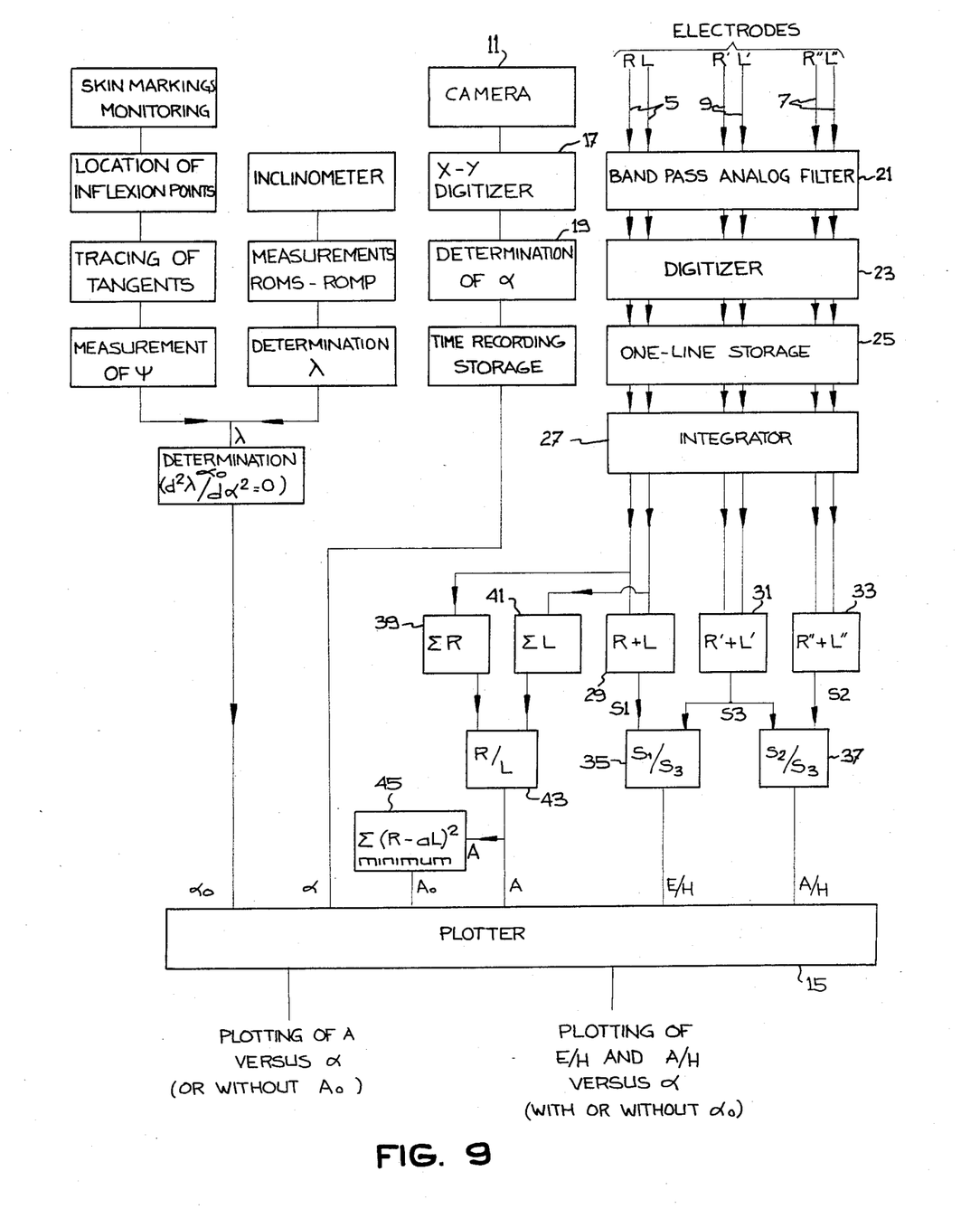
FIG. 9 is a block-diagramm of the electronic part of the equipment shown in FIG. 1.

As shown in FIG. 1, the equipment 1 necessary for the detection of mechanical abnormality or injury in the lumbar spine of a patient P and for the identification of the so detected abnormality or injury as being of the compression or torsion type comprises a processing unit 13 connected to a plotter 15. A block diagramm of this processing unit 13 is shown in FIG. 9.

The equipment 1 also comprises a first set of surface electrodes 5 fixable onto the patient P in a bilateral and symmetrical manner with respect to his spine for measuring the electromyographic activities of the erectores (sairospinalis, multifidus, etc . . . ) of this patient while he is flexing forward in his median plane M and pulling up a small load L. The load to be pulled up may consist of a small weight to be lifted up, as shown in FIG. 1, or of a mere chain or elastic ship fixed to the ground.

Another set of surface electrodes 7 is fixed onto the patient P in a bilateral and symmetrical manner with respect to his spine for measuring the electromyographic activities of the abdominals of said patient while the same is flexing forward in the median plane and pulling up the small load L. Advantageously, these electrodes 7 may be fixed onto the triangles of Petit of the patient P in order to record the EMG activities of the internal oblique of said patient. In this particular case the so recorded activities can be used as an indicative value of the activity of all of the abdominals.

In addition, a further set of surface electrodes 9 are fixed on the patient P behind his thighs to measure the electromyographic activities of the Gluteus Maximus of the patient. The so measured activities are in practice used as representative of the activities of all of the hip-extensors of the patient.

Figures 3A, 3B:
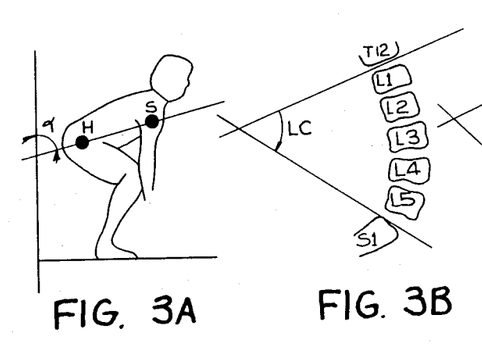
Figure 3C:
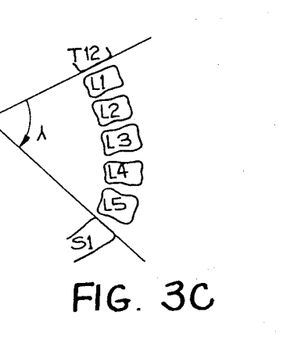

Means including a stop-action camera 11 are provided for measuring the angle of flexion $\alpha$ of the patient, the angle $\alpha$ being the dihedral angle between a plane passing through the hips and shoulders of the patient and the vertical plane parallel to the frontal plane of said patient (see FIG. 3a). As shown in FIG. 9, the stop-action camera 11 is connected to an X-Y digitizer 17 for digitizing the relative positions of the shoulders and hips of the patient in the median plane. This digitizer 17 is connected to means 19 known per se for determining the angle $\alpha$ between a line passing through the digitized positions and a vertical line. As means 19, use can be made, for example, of the non-contact three dimensional digitizing system and program sold under the tradename WATSMART by NORTHER DIGITAL INC. of Waterloo, Ontario.

C. COLLECTION AND TREATMENT OF THE INFORMATION (a) Determination of the EMG activities versus the angle of flexion $\alpha$ After fixation of the surface electrodes 5, 7 and 9 onto the erectores, abdominals and hip-extensors of the patient P in a bilateral and symmetrical manner with respect to his spine, the patient P is requested to execute a simple weight lifting symmetrical task with the load L which is preferably lower than 10 kg. During the lift, the EMG activity is monitored as explained hereinabove, together with the attitude of the patient.

As shown in FIG. 9, all the measured EMG signals are bandpass analog filtered in the range of 10 to 300 Hz with a filter 21 and then digitized at 1 000 samples per second (12 bits accurately) with a digitizer 23. They are subsequently stored on-line on digital disks 25. When the task is complete, the data is available for recall and processing. The artifacts may be routinely reduced and datas smoothed by using a combination of linear and non linear filtering algorithms. This gives an envelope of the measured muscle activity as a function of time. Of course, a greater degree of sophistication is possible because, in this particular case, the theory predicts the shape and form of EMG signals. Use can be made of this information to define more accurately the true muscle responses.

The activity signals measured on the right and left sides of the patient by each pair of electrodes 5, 7 and 9 are thereafter integrated with an integrator 27 in order to determine the magnitude of muscle activity prior to processing the so recorded activity in order to calculate the relative variation in activities of the erectores versus the hip extensors (E/H ratio) and of the Internal Obliques versus the hip extensors (A/H ratio), and simultaneously calculate the amount of asymmetry (a) between the recorded EMG activity measured on the right side of the patient and the recorded EMG activity measured in the left side of the patient.

As shown in FIG. 9 a first means 29 is used for toting up the integrated signals R and L measured by the surface electrodes 5 fixed in the lumbar zone of the patient at a given time. Second means 31 are also provided for toting up the integrated signals R' and L' measured by the surface electrodes 9 fixed on the triangles of Petit of the patient at the same given time whereas third means 33 are provided for toting up the integrated signals R" and L" measured by the surface electrodes 9 fixed behind the thighs of the patient as the same given time.

The output signals $S_1$ and $S_3$ of the first and second toting means 29 and 31 as supplied to a first divider 35 where $S_1$ is divided by $S_3$ to obtain a first ratio. The output signal $S_2$ of the third toting means 33 is supplied with the output signal $S_3$ of the second means 31 to a second divider 37 where $S_2$ is divided by $S_3$ to obtain a second ratio. These two ratios which are proportional to the desired ratios E/H and A/H respectively, are then plotted versus $\alpha$ by the plotter 15.

Simultaneously to the above described processing, the integrated signals R measured by the surface electrodes 5 fixed to the back of the patient on the right side thereof with respect to the median plane of said patient at a given time are toted up by toting means 39 whereas the integrated signal L measured by the symmetrical surface electrodes 5 fixed onto the back of the patient on the left side thereof with respect to his median plane are toted up by toting means 41. The output signals of the toting means 39 and 41 are supplied to a divider 43 where $\Sigma R$ is divided by $\Sigma L$. The obtained ratio of this division is, in practice, equal to the amount of asymmetry $<<a>>$.

In order to determine the amount of irreducible asymmetry $<<a_o>>$ between the right and left sides of the patient, means 45 may be provided for minimizing with respect to $<<a>>$ the sum of the square of the difference $(R-aL)$ measured during the flexion of the patient.

Once again, the calculated amount of asymmetry "a" and the determined amount of irreducible asymmetry "$a_o$" are supplied to the plotter 15 so that they may be plotted as a function of $\alpha$.

Of course, during this measurement, the attitude of the patient is synchronized with the acquisition of EMG data by using the stop-action camera 11 at four frames per second. The marked positions of the shoulders and hips are digitized with the X-Y digitizers 17. This procedure permits to obtain the EMG at any hip-shoulder attitude, which is defined by the angle $\alpha$. The skin motion has a negligeable effect on the determination of the angle $\alpha$.

Figure 5A:
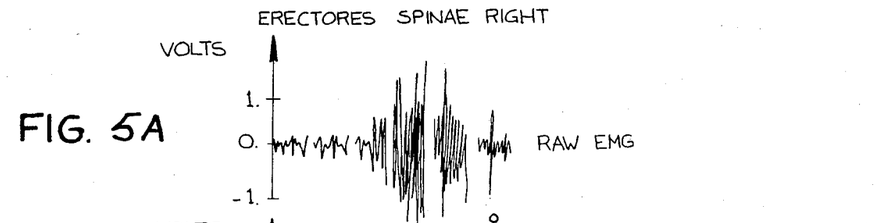
Figure 5B:
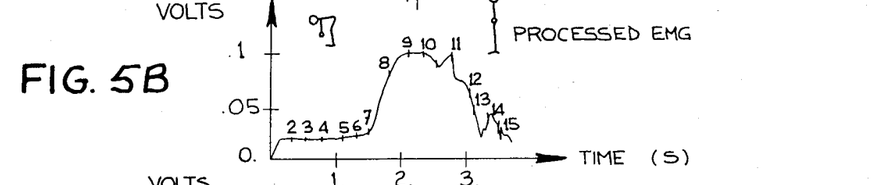
Figure 5C:
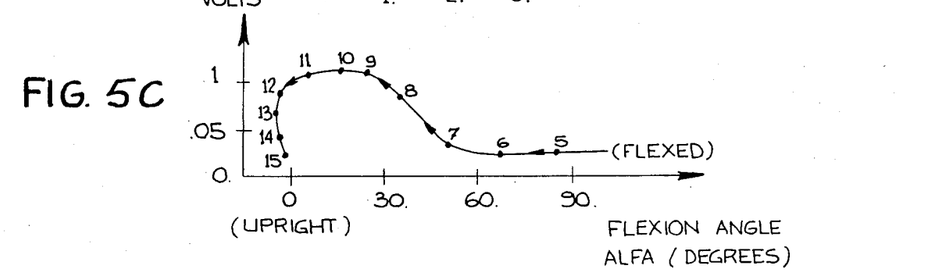

A typical measurement of EMG and its subsequent processing is shown in FIGS. 5(a), (b), (c). In FIG. 5(a) the EMG of the erectores spinae is shown versus time. This particular case, the signal was band filtered and amplified between 10 and 300 Hz. The measuring electrode was located at the level of vertebra $L_3$ at 5 cm to the right of the spinous process of the vertebra.

FIG. 5(b) shows the processes EMG signal versus time. The numbers superimposed onto the curve indicates the instant at which photographs were taken. This permits the measurement of the flexion angle $\alpha$.

Last of all, FIG. 5(c) shows the processed EMG 30 activity versus $\alpha$. This FIG. 5(c) clearly shows that, from zero 45°, the external moment in the lumbar zone is balanced by the action of the muscles. During this first arc of motion, the spine unfolds or straightens out. At approximatively 45° the spine is sufficiently flexed to permit the midline ligament to be set under tension. When this is done, the power of the hip extensors is transmitted directly to the upper extremities. In this particular case, there is no more need for an activity of the erectores spinae.

It can be appreciated that a stiff spine will not permit the full use of the posterior ligamenteous system instead of the erectores spinae. Consequently, the erectores spinae would have the work more and therefore increase the level of stress that the spine must take with the attendant higher probability of failure.

(b) Measurement of the lumbo-sacral curve angle

As aforesaid, an healthy individual naturally switches the balancing of a load from his muscle to his ligaments in order to reduce the stress level which his spine has to sustain. As such a switch-over cannot be executed until the midline ligaments are set under tension, it may be of great interest to know the precise time at which such a switch-over occurs in order to better interpret the EMG data. It is therefore of great interest to determine the angle of flexion $\alpha_o$ at which the spine is sufficiently flexed for the midline to be activated.

Preliminary investigation conducted by the inventor has shown that $\alpha_o$ is a function of the weight to be lifted. The same investigation has also shown that, when the weight to be lifted is small, the individual has considerable freedom in determining at which point it will switch over from muscles to ligaments. This is due to the fact that the midline ligaments can be set under tension by a combination of spine flexion and pelvis rotation.

As the hip-shoulder angle $\alpha$ does not describe this particular combination, it is difficult to obtain $\alpha_o$ simply by monitoring $\alpha$. The determination of $\alpha_o$ must be made separately and this can be done in practice as follows.

According to a first invasive method, the determination of $\alpha_o$ can be accomplished by measuring the change in lumbar spine motion in lateral radiographs between upright relaxed stance and full forward relaxed flexion. The sacro-lumbar curve referred to hereinabove is the angle LC shown in FIG. 3(b) between the lower end plate of vertebrae $T_{12}$ and the upper end plate of vertebra $S_1$. Geometrical considerations dictate that the sacro-lumbar curve angle depends on the ligament length. Because the midline ligament is a passive structure, its length is determined by the tension it has to sustain, provided that this tension is not maintained for a long time. Therefore, the sacro-lumbar curve angle LC characterized the ligament tension. As the subject lifts a weight, the sacro-lumbar angle increases slowly until the tension of the midline ligaments drops to zero. From then on, the sacro-lumbar curve increases rapidly. The sudden change in sacro-lumbar curve marks the $\alpha_o$ angle.

Figure 4:
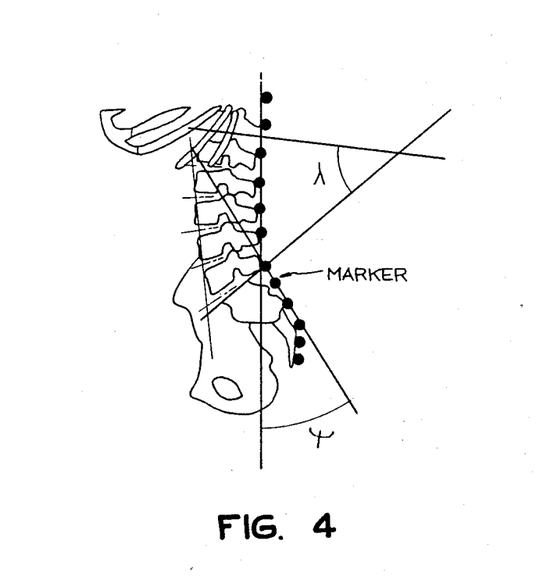
FIG. 4 is a schematic representation of the relative positions of a strain of markers attached to the skin along the spine in the saggital plate, said markers being used to determine the angles $\lambda$, $\Omega$ and $\alpha_o$.

According to a second non-invasive method, the lumbo-sacral angle $\lambda$ can be measured in a non-invasive manner by detachably fixing a string of skin markers to the skin of the back of the patient in the midline of his spine from at least thoracic vertebra $T_{10}$ down to at least sacral vertebra $S_3$ (see FIG. 4). The skin markers may consist of visible dots, in which case their relative positions may be monitored with a high resolution TV camera. Alternatively, they may consist of ultrasonic emitters, in which case their relative positions may be monitored with a set of three ultrasonic microphones. According to a third method, the skin markers may consist of small reflectors in which case a laser beam may be used as visualisation equipment.

In all cases, when the individual flexes forward, the skin markers move with the corresponding change in the lumbo-sacral angle $\lambda$ and may be monitored (see FIG. 9). Mathematical curve fitting allows the identification of the inflexion point on the curve. By tracing tangents to this inflexion point, it is possible to determine an angle $\psi$ between said tangents, which angle $\psi$ is directly related to the lumbo-sacral angle $\lambda$ (see FIG. 4).

This dynamic technique of angle determination is relatively insensitive to change in skin markers relative to the underlying bony landmarks. The markers stay in the midline as they move with the skin along the main axis of the spine and therefore skin motion in this direction is not important in the determination of the angle. Displacements in the saggital plane between markers and bony points could make a difference at the sacro-lumbar joint where there is a greatest thickness of interposed fat. However, it is in this region that the saggital plane displacement of markers create the least error in the angle determination.

In practice, the angle $\psi$ may be used directly instead of the lumbo-sacral angle $\lambda$, since the present invention is only concerned with timing and not with absolute values.

According to a third, non-invasive method the measurement of $\alpha_o$ can be carried out by pressing a pair of inclinometers against the lumbar spine of the patient. By measuring with these inclinometers the range of motion of the spine (ROMS) and the range of motion of the pelvis (ROMP) when the patient is flexing forward (see FIG. 9), it is possible to determine the lumbo-sacral angle $\lambda$. Indeed, as the subject flexes forward, the ROMS varies at the spine straightens. When the spine is straight, the ROMS stops varying, although $\alpha$ continues to vary (because the subject continues to bend forward since his pelvis rotates). The value of $\alpha$ at which ROMS stops varying defines the angle $\alpha_o$. This particular way of determining the angle $\lambda$ and deriving therefrom the angle $\alpha_o$ is disclosed by T. G. Mayer et al in their article <<The use of non-invasive techniques for quantification of spinal range of motion in normal subjects and chronic low back dysfunction patient>>, Spine, volume 9, No. 6, 1984, pp 588 to 595.

As explained hereinabove, the measurement of the lumbo-sacral angle $\lambda$ permits to obtain the angle $\alpha_o$ at which the lordosis of the patient's spine is eliminated when the patient is pulling up the small load, said angle $\alpha_o$ being the one at which the variation of the rate of change of $\lambda$ versus $\alpha$ is maximum.

As also indicated hereinabove, the so determined angle $\alpha_o$ can be used as a parameter interpretation in the mathematical model, said angle $\alpha_o$ indeed corresponding to the angle at which the patient will switch the balancing of the load being pulled up from his muscles to his ligaments in order to reduce the stress level which his spine has to sustain.

(c) Reduction of data

Using the above described equipment, it is possible to calculate the relative variations of the erectores and abdominals versus the hip extensors (E/H and H/H ratios). By plotting these ratios versus the angle of flexion $\alpha$, it is possible to distinguish patients suffering a compression injury from those having an healthy spine. In order to facilitate the interpretation of the plotted curves, the critical angle $\alpha_o$ can also be plotted and used as a reference.

Using the same equipment, it is possible to determine the degree of asymmetry and detect the presence of a torsional injury by calculating the parameter <<a>> and by measuring any discrepancy of <<a>> versus $\alpha$. In order to facilitate this interpretation of the plotted curve, <<$a_o$>> can be calculated to determine the standard deviation of the spine of the patient.

For the various reasons explained hereinabove, the observation of a high A/H ratio which corresponds to an extensive use of the abdominals, with a simultaneous observation of the significant delay in the detection of the sharp variation of the E/H ratio at a given angle $\alpha_o$ or of no variation at all of said E/H ratio when the patient is pulling up a small load, indicates that the patient cannot relax his erectores at the beginning of the lift. Such a refusal indicates in turn that the patient has difficulty to flex his spine and therefore has a joint injury of the compression or torsion type. In addition, the observation of the significant variation of <<a>> when $\alpha$ varies, that is during the lift of a small weight, indicates that the injury in the lumbar spine is of the torsional type rather than of the compression type.

(i) Healthy response

A healthy response that can be obtained from a patient lifting a small load is variable as shown in FIG. 7 which shows healthy EMG responses as a function of different loads to be lifted (10, 15, 20 and 25 kg). The consistency of each set of curves shown in FIG. 7 is eYidence that the subject controls the share of moment supported by the muscles. Curves (A) show an early extensor shut off. In this case, the spine flexion is delayed as long as possible. Curve (B) shows late extensor shut-off in this case, the spine flexion is delayed as long as possible. Curves (C) show an intermediate strategy. Last of all, curves (D) is an overlay of curves A, B and C for a 25 kg load. As can be seen, the muscle relaxation phenomena and the variation of the switch-over from muscle to ligament are evident and not scattered.

The apparent variation in the EMG pattern is due to the ability of the individual to alter his pelvis angle in order to control the angle flexion at which the ligaments are introduced. The theory relates the onset of ligaments to the lumbo-sacral angle λ. Hence, the variation noted is not true scatter and does not represent a true variation in spine mechanics.

(ii) Abnormal response

An abnormal response is substantially different from a normal one in several respect. First, the degree of symmetry in the data collected by the right and left electrodes is poor. Secondly, the spine is not completely flexed, such being apparent from the fact that the erectores are active until the weight is on the floor. Third, the variation is muscular response during the lift is not smooth.

Figure 8A:
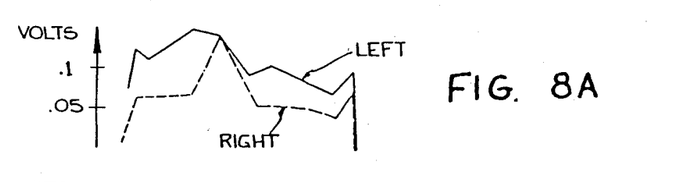
Figure 8B:
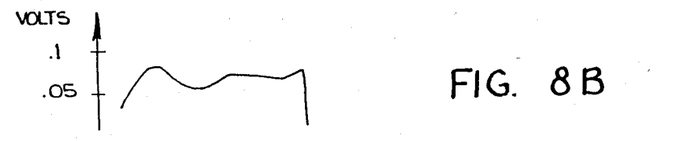
Figure 8C:
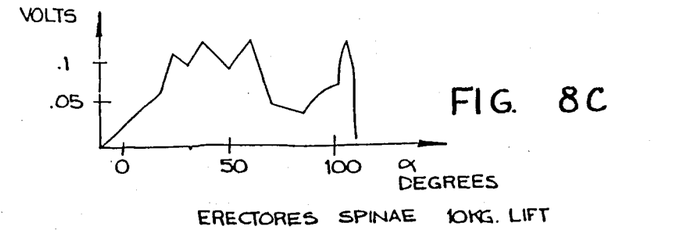

FIG. 8 gives examples of such abnormal responses. More particularly, FIG. 8(A) shows an asymmetric response. FIG. 8(B) shows a response in the case of a lack of muscle relaxation. FIG. 8(C) shows an irregular response (see, by way of comparison, FIG. 5(C)).

As can now be easily understood, the ability to identify the control system of an individual combined with the kinematics of a symmetrical task such as a symmetrical weight lifting advantageously permits:

the assessment of the stress induced by a task of an individual, as a function of the amount of tuning necessary to minimize the differences between the observed and calculated pattern;

the observation of an individual on different occasions over a period of time; and the detection of injury and state of recovery;
the identification of the type of injury;
the amount of stress induced by any given task.

Although the masculine pronoun has been used exclusively hereinabove, it has to be interpreted as including the feminine.

I claim:

1. A method for the detection of mechanical injuries in the lumbar spine of a patient and the identification of said injuries as being of the compression and/or torsional type, comprising the steps of:
    (a) fixing a first pair of surface-electrodes onto the back of the patient in a bilateral and symmetrical manner with respect to his spine in the lumbar zone, in order to record the electromyographic (EMG) activities of erectores of said patient;
    (b) fixing a second pair of surface-electrodes in a bilateral manner onto the triangles of Petit of said patient in order to record the EMG activity of the Internal Oblique of said patient;
    (c) fixing a third pair of surface-electrodes in a bilateral manner behind the thighs of said patient in order to record the EMG activity of the hip extensors of said patient;
    (d) measuring with said surface-electrodes the muscle activity of the patient while he is flexing forward in the median plane and pulling up a small load, and independently recording the EMG activities measured by each of said surface electrodes as a function of time;
    (e) simultaneously to step (d), measuring the angle of flexion $\alpha$ of the patient, said angle $\alpha$ being the dihedral angle between a plane passing through the hips and shoulders of said patient and a vertical plane parallel to the frontal plane of said patient, and recording said angle $\alpha$ as a function of time;
    (f) processing the recorded EMG activities measured on the patient to calculate the relative variations in activities of the erectores versus the hip extensors (E/H ratio) and of the Internal Oblique versus the hip extensors (A/H ratio) and plotting said E/H and A/H ratios versus $\alpha$; and
    (g) further processing said recorded EMG activities measured on the patient to calculate the amount of assymmetry <<a>> between the recorded EMG activities measured on the right side of the patient and the recorded EMG activities measured on the left side of said patient, and plotting <<a>> versus $\alpha$;
    wherein the observation of a high A/H ratio which corresponds to an extensive use of the abdominals, with the simultaneous observation of a significant delay in the detection of a sharp variation of the E/H ratio at a given angle $\alpha_o$ or of no variation at all of said E/H ratio when the patient is pulling up the small load, indicate that the patient cannot relax his erectores at the beginning of the lift, such a refusal indicating in turn that the patient has difficulty to flex his spine and therefore has a joint injury of the compression or torsional type; and
    wherein the observation of a significant variation of <<a>> when $\alpha$ varies, that is during the lift of the small load, indicates that the joint injury in the lumbar spin is of the torsional type.

2. The method of claim 1, wherein the measurement of $\alpha$ is carried out by:
    monitoring and recording with a stop-action camera the relative positions in the median plane of the shoulders and hips of the patient while the same is flexing forward;
    digitizing with an X-Y digitizer said relative positions;
    determining the angle between a line passing through said digitized positions and a vertical line; and
    using the so determined angle as angle $\alpha$.

3. The method of claim 2, wherein the relative positions of the shoulder and hips are monitored at least twice per second.

4. The method of claim 2, wherein the EMG activity processing comprising the preliminary step of:
    integrating the activity signals measured by the surface-electrodes to determine the magnitude of the muscle activity.

5. The method of claim 4, wherein the calculation of the E/H and A/H ratios at a given time is carried out by:
    toting up the integrated signals the surface electrodes fixed in the lumbar zone of the patient at said given time to obtain a first toted-up signal $S_1$;
    toting up the integrated signals measured by the surface electrodes fixed on the triangles of Petit of the patient at said given time to obtain a second toted-up signal $S_2$;
    toting up the integrated signals measured by the surface electrodes fixed behind the thighs of the patient at said given time to obtain a third toted-up signal $S_3$;
    dividing $S_1$ by $S_3$ to obtain a first ratio;
    dividing $S_2$ by $S_3$ to obtain a second ratio; and
    using the first and second ratios as E/H and A/H ratios, respectively.

6. The method of claim 5, wherein the calculation of the amount of assymmetry <<a>> at a given time is carried out by:
    toting up the integrated signals measured by one of the surface electrodes fixed on the right side of the patient with respect to the median plane of said patient at said given time to obtain a signal R;

toting up the integrated signals measured by one or the surface electrodes fixed on the left side of the patient with respect to the median plane of said patient at said given time to obtain a signal L; and dividing signal R by signal L, the obtained ratio being equal to the amount <<a>> of assymmetry at said given time to which corresponds a given angle α.

7. The method of claim 6, wherein the calculation of the amount of assymmetry <<a>> further comprises the steps of:

minimizing with respect to <<a>> the sum of the square of the differences (R−aL) measured during flexion of the patient to determine the amount $\alpha_o$ of irreductible assymmetry between the right and left sides of the patient; and using said amount $\alpha_o$ to appreciate the variation of <<a>> when α varies.

8. The method of claim 7, wherein the surface electrodes used for calculating the amount of assymmetry <<a>> and for determining <<$a_o$>> are those fixed onto the back of the patient to record the EMG activities of his erectores.

9. The method of claim 8, wherein the EMG activity processing comprises the additional preliminary steps of:

filtering in the range of 10 to 300 Hz the activity signals measured by the surface-electrodes with a bandpass analog filter;

digitizing at 1000 samples per second (12 bits accuracy) the filtered signals; and storing on line the digitized signals for recall and further processing.

10. The method of claim 2, comprising the additional steps of:

(h) measuring the lumbo-sacral angle λ, said angle λ being the angle between the bissector of the $L_5$-$S_1$ disc and the bissector of the $T_{12}$-$L_1$ disc of the patient; and (i) using said measured angle λ to determine the angle $\alpha_o$ at which the lordosis of the patient's spine is eliminated when said patient is pulling up the small load, said elimination corresponding to a switching made by the patient of the balancing of the load being pulled up from his ligaments to his muscles in order to reduce the stress level which the spine has to sustain, said angle $\alpha_o$ which is the very one at which a sharp variation of the E/H ratio should be detected, being the angle a at which the variation of the rate of change of λ versus α is maximum.

11. The method of claim 10, wherein the measurement of λ is carried out by:

taking lateral radiographs of the patient while he is flexing forward in his median plane and pulling up the small load.

12. The method of claim 10, wherein the measurement of λ is carried out in a non-invasive manner by:

detachably fixing a string of skin-markers to the skin of the back of the patient in the midline of his spine from at least thoracic vertebra $T_{10}$ down to at least sacral vertebra $S_3$;

monitoring with a high resolution T.V. camera the relative positions of said skin-markers in the median plane of the patient while the same is flexing forward, said skin-markers altogether defining a curve with an inflexion point;

locating the inflexion point on the monitored curve and tracing tangents to said inflexion point;

measuring the angle ψ between said tangents; and using said angle ψ as sacrolumbar angle λ.

13. The method of claim 10, wherein the measurement of λ is carried out in a non-invasive manner by:

pressing a pair of inclinometers against the lumbar spine of the patient;

measuring with said inclinometers a range of motion of the spine (ROMS) and a range of motion of the pelvis (ROMP) when the patient is flexing forward; and deriving from said ranges the lumbo-sacral angle λ of the patient.

14. An equipment for the detection of mechanical injuries in the lumbar spine of a patient and the identification of said injuries as being of the compression and/or torsional type, said, equipment comprising:

a first pair of surface-electrodes fixable onto the back of the patient in a bilateral and symmetrical manner with respect to his spine in the lumbar zone in order to record the electromyographic (EMG) activities of the erectores of said patient;

a second pair of surface electrodes fixable in a bilateral manner onto the triangles of Petit of the patient in order to record the EMG activity of the Internal Oblique of said patient;

a third pair of surface electrodes fixable in a bilateral manner behind the thighs of the patient in order to record the EMG activity, of the hip extensors of said patient;

means connected to said first, second and third pairs of surface electrodes for measuring the EMG activity of the patient with said pairs of surface electrodes while he is flexing forward in the median plane and pulling up a small load;

means connected to said EMG activity measuring means for independently recording the EMG activity measured by each of said surface electrodes as a function of time;

means for mesuring the angle of flexion α of the patient, said angle α being the dihedral angle between a plane passing through the hips and shoulders of the patient and the vertical plane parallel to the frontal plane of said means connected to said angle measuring means for recording the measured angle as a function of time;

means connected to said EMG activity recording means for processing the recorded EMG activities measured on the patient to calculate the relative variations in activities of the erectores versus the hip extensors (E/H ratio) and of the Internal Oblique versus the hip extensors (A/H ratio);

means connected to said processing means and said angle α recording means for plotting said E/H and A/H ratios versus α;

means connected to said EMG activity recording means for further processing the recorded EMG activities measured on the patient to calculate the amount of assymmetry "a" between the recoded EMG activities measured on the right side of the patient and the recorded EMG activities measured on the left side of said patient; and means connected to said further processing means for plotting "a" versus α.

15. The equipment of claim 14, wherein said means for measuring the angle of flexion comprises:

stop action camera means for monitoring, in the median plane, the relative positions of the shoulders and hips of the patient when the same is flexing forward;

X-Y digitizer means connected to said camera means for digitizing said relative positions; and means connected to said X-Y digitizer for determining the angle between a line passing through said digitized positions and a vertical line, said determined angle being used as angle $\alpha$.

16. The equipment of claim 15, wherein said means for processing the EMG activities also comprises:

means for integrating the activity signals to determine the magnitude of the muscle activity.

17. The equipment of claim 16, wherein said means for processing the EMG activities comprises:

means for toting up the integrated signals measured by the surface electrodes fixed in the lumbar zone of the patient at a given time, said toting means giving a signal $S_1$;

means for toting up the integrated signals measured by the surface electrodes fixed on the triangle of Petit of the patient at said given time, said toting means giving a signal $S_2$;

means for toting up the integrated signals measured by the surface electrodes fixed behind the thighs of the patient at said given time, said toting means giving a signal $S_3$;

means for dividing $S_1$ by $S_3$ to obtain a first ratio; and means for dividing $S_2$ by $S_3$ to obtain a second ratio; said first and second ratios being used as E/H and A/H ratios.

18. The equipment of claim 17, wherein said means for further processing the EMG activities comprises:

means for toting up the integrated signals measured by the surface electrodes fixed onto the back of the patient on the right side thereof with respect to the median plane of said patient at a given time, said toting means giving a signal R;

means for toting up the integrated signals measured by the symmetrical surface electrode fixed onto the back of the patient on the left side thereof with respect to his median plane at said given time, said toting means giving a signal L; and a divider means for dividing R by L, the obtained ratio being equal to the amount of assymmetry $<<a>>$ at said given time to which correspond an angle $\alpha$.

19. The equipment of claim 18, wherein said means for further processing the EMG activities also comprises:

means for minimizing with respect to $<<a>>$ the sum of the square of the differences (R−aL) measured during flexion of the patient to determine the amount of irreductible assymmetry $<<a_o>>$ between the right and left sides of the patient.

20. The equipment of claim 19, wherein said means for processing the EMG activities further comprises:

band pass analog filter means for filtering in the range of 10 to 300 Hz the activity signals measured by the surface electrodes;

means for digitizing at 1000 samples per second (12 bits accuracy) the filtered signals; and means for storing on line the digitized signals for recall and further processing.

21. (amended) The equipment of claim 15, further comprising:

means for measuring the lumbo-sacral angle $\lambda$, said angle $\lambda$ being the angle between the bissector of the $L_5$–$S_1$ disc and the bissector of the $T_{12}$–$L_1$ disc of the patient; and means connected to said angle $\alpha$ measuring means and said angle $\lambda$ measuring means for determining the angle $\alpha_o$ which is the angle at which a sharp variation of the E/H ratio should be detected, being the angle $\alpha$ at which the variation of the rate of change of $\lambda$ versus $\alpha$ is maximum.

22. The equipment of claim 21, wherein said means for measuring the lumbo-sacral angle $\lambda$ comprises:

a plurality of skin-markers attachable to the skin of the back of the patient to form a string along the midline of his spine from at least thoracic vertebra $T_{10}$ down to at least sacral vertebra $S_3$;

high resolution T.V. camera means for monitoring the relative positions of said skin-markers in the median plane of the patient while the same is flexing forward, said skin-markers all together defining a curve with an inflexion point;

means for locating the inflexion point on the monitored curve;

means for tracing tangents to said inflexion point; and means for measuring the angle $\psi$ between said tangents, said angle $\psi$ between said tangent being used as angle $\lambda$.

23. The equipment of claim 21, wherein said means for measuring the lumbo-sacral angle $\lambda$ comprises:

a pair of inclinometers to be pressed against the lumbar spine of the patient;

means for measuring with said inclinometers a range of motion of the spine (ROMS) and a range of motion of the pelvis (ROMP) when the patient is flexing forward; and means connected to said ROMS and ROMP measuring means for deriving from said ranges the lumbo-sacral angle $\lambda$ of the patient.

* * * * *